(12) United States Patent
Tucker et al.

(10) Patent No.: US 10,357,653 B2
(45) Date of Patent: Jul. 23, 2019

(54) DEVICE FOR INCREASING MICROCIRCULATION (71) Applicant: Sky Medical Technology Ltd., Cheshire (GB)

(72) Inventors: Arthur Tudor Tucker, London (GB); Duncan Shirreffs Bain, Kings Langley (GB)

(73) Assignee: Sky Medical Technology Ltd., Cheshire (GB)

( * ) Notice: Subject to any disclaimer, the term of this patent is extended or adjusted under 35 U.S.C. 154(b) by 259 days.

(21) Appl. No.: 14/410,889

(22) PCT Filed: Jun. 25, 2013

(86) PCT No.: PCT/GB2013/051665
§ 371 (c)(1),
(2) Date: Dec. 23, 2014

(87) PCT Pub. No.: WO2014/001778
PCT Pub. Date: Jan. 3, 2014

(65) Prior Publication Data
US 2015/0182746 A1  Jul. 2, 2015

(30) Foreign Application Priority Data
Jun. 26, 2012 (GB) .................................. 1211316.3

(51) Int. Cl.
*A61F 5/05* (2006.01)
*A61N 1/04* (2006.01)
(Continued)

(52) U.S. Cl.
CPC ............ *A61N 1/36003* (2013.01); *A61F 5/05* (2013.01); *A61N 1/0452* (2013.01); *A61N 1/321* (2013.01)

(58) Field of Classification Search
CPC .. A61F 5/05; A61F 5/01; A61F 5/0106; A61F 5/0111; A61F 5/0123;
(Continued)

(56) References Cited

U.S. PATENT DOCUMENTS 3,911,910 A * 10/1975 Oesau ................ A61N 1/36003
602/2
4,445,518 A  5/1984 Eggli et al.
(Continued)

FOREIGN PATENT DOCUMENTS

GB  1 527 233  10/1978
GB  2 426 930 A  12/2006
(Continued)

OTHER PUBLICATIONS

PCT/GB2013/051665, Aug. 26, 2013, International Search Report.
(Continued)

*Primary Examiner* — Alireza Nia
*Assistant Examiner* — Rachel A Berezik
(74) *Attorney, Agent, or Firm* — Wolf, Greenfield & Sacks, P.C.

(57) ABSTRACT

A method and device for increasing microcirculation in the lower limb are described. The device includes a means for immobilizing the limb, for example a plaster cast, and an electrical stimulation device, which applies electrical stimulation to opposed leg muscles such that antagonistic and agonistic muscle groups contract near simultaneously, resulting in near isometric contraction. The combination of this contraction and the leg restraint have been found to markedly increase blood circulation and in particular microcirculation in the limb.

9 Claims, 3 Drawing Sheets

(51) Int. Cl.
*A61N 1/32* (2006.01)
*A61N 1/36* (2006.01)

(58) Field of Classification Search
CPC ............ A61F 5/0585; A61F 2007/0001; A61F 5/05841; A61F 5/05825; A61F 13/04; A61F 13/06; A61F 13/061; A61F 13/066; A61F 2013/00361; A61F 2013/00621; A61F 13/041; A61N 1/36003; A61N 1/0452; A61N 1/321; A61N 1/04; A61N 1/0456; A61N 1/32; A61N 1/36
USPC ................ 602/2; 607/1, 2, 145, 146, 147
See application file for complete search history.

(56) References Cited

U.S. PATENT DOCUMENTS

| | | | |
|---|---|---|---|
| 4,586,495 A * | 5/1986 | Petrofsky | A61N 1/36003 |
| | | | 482/1 |
| 4,976,264 A | 12/1990 | Petrofsky | |
| 5,674,262 A * | 10/1997 | Tumey | A61H 9/0078 |
| | | | 128/DIG. 20 |
| 6,282,448 B1 * | 8/2001 | Katz | A61N 1/321 |
| | | | 607/149 |
| 7,177,705 B2 | 2/2007 | Cohen | |
| 2002/0016618 A1 * | 2/2002 | Da Silva | A61N 1/0472 |
| | | | 607/72 |
| 2004/0236384 A1 * | 11/2004 | Dar | A61N 1/0452 |
| | | | 607/48 |
| 2004/0249432 A1 | 12/2004 | Cohen | |
| 2005/0043659 A1 | 2/2005 | Challis et al. | |
| 2007/0060975 A1 | 3/2007 | Mannheimer et al. | |
| 2008/0306325 A1 * | 12/2008 | Burnett | A61N 2/02 |
| | | | 600/13 |
| 2010/0262052 A1 * | 10/2010 | Lunau | A61B 5/6828 |
| | | | 602/5 |
| 2011/0178447 A1 * | 7/2011 | Helfer | A61F 5/01 |
| | | | 602/2 |
| 2012/0041513 A1 | 2/2012 | Tucker et al. | |
| 2012/0053655 A1 * | 3/2012 | Bain | A61N 1/205 |
| | | | 607/48 |

FOREIGN PATENT DOCUMENTS

| | | | |
|---|---|---|---|
| JP | S48-035151 | 3/1973 | |
| JP | H11-505161 | 5/1999 | |
| JP | 2009-112380 A | 5/2009 | |
| RU | 2105538 C1 | 2/1998 | |
| RU | 2365388 C2 | 8/2009 | |
| WO | WO 2006/054118 | 5/2006 | |
| WO | WO 2006054118 A1 * | 5/2006 | ......... A61N 1/36003 |
| WO | WO 2010/070332 | 6/2010 | |
| WO | WO 2011/158018 A1 | 12/2011 | |

OTHER PUBLICATIONS

PCT/GB2013/051665, Dec. 31, 2014, International Preliminary Report on Patentability.
International Search Report for PCT/GB2013/051665 dated Aug. 26, 2013 (4 pages).
International Preliminary Report on Patentability for PCT/GB2013/051665 dated Dec. 31, 2014 (8 pages).
Japanese Examiner's Report dated Apr. 3, 2017 in connection with Japanese Application No. 2015-519330.

* cited by examiner

DEVICE FOR INCREASING MICROCIRCULATION

RELATED CASE INFORMATION

This application is a 371 U.S. National Stage Application of International Application No. PCT/GB2013/051665, filed on Jun. 25, 2013, which claims priority to Great Britain application no. 1211316.3, filed on Jun. 26, 2012.

FIELD OF THE INVENTION

The present invention relates to a method and kit for improving blood flow, particularly microcirculation, in the lower limbs.

BACKGROUND TO THE INVENTION

A method and device for improving blood circulation in lower limbs of a patient have previously been described in our international patent application WO2006/054118. The contents of this publication are incorporated herein by reference.

This publication describes a device for improving blood circulation in a lower limb of a patient, the device comprising at least one electrode for administering an electrical stimulus to opposed leg muscles of a patient; a power supply connectable to the electrode; and a control means for activating the electrode to administer an electrical stimulus to the muscles sufficient to cause the muscles to contract isometrically. The stimulus may be applied directly or indirectly to the muscle. The muscles may be calf muscles, or may be the ankle and/or foot musculature.

The device operates by providing electrical stimulation to the lateral popliteal nerve in the region of the popliteal fossa. Additional stimulation may be applied to the medial popliteal nerve. Stimulation of the lateral popliteal nerve, in the region of the popliteal fossa, has the advantage of initiating the contraction of both posterior and anterior lower limb muscle groups. Such simultaneous stimulation results in isometric contraction; hence the ankle and knee joints would not be typically mobilised, while the muscle contraction is however sufficient to mobilise the so-called "calf pump" which aids in improving blood circulation in the lower limb. Stimulation of the lateral popliteal also elicits contraction of the foot muscles and hence the so-called "foot-pump" thereby further stimulating emptying of venous blood and enhancing blood flow. Additionally, the surprising advantage of selective stimulation of the lateral popliteal nerve is that the resultant muscular contractions are entirely compatible with standing and walking. An additional benefit of this mode of indirect stimulation is the involvement of the muscles in the sole of the foot, which have been shown to contribute substantially to clearance of blood from the lower leg.

In view of the fact that such isometric stimulation arising from simultaneous contraction of anterior and posterior muscle groups does not result in gross limb movement, and is intended to be compatible with walking, it has not hitherto been considered desirable to apply such stimulation to immobilised limbs.

However, we have now surprisingly discovered that application of isometric stimulation to an immobilised limb dramatically improves the increase in blood flow, and in particular promotes microcirculation in the limb.

U.S. Pat. No. 4,586,495 to Petrofsky describes a device for stimulating muscular activity in a patient with spinal cord injury. The device includes an external brace for applying to a leg, and a number of electrical stimulators. The leg muscles are stimulated, and the brace restrains movement. The system alternately stimulates agonist and antagonist muscles, which is necessary to allow the brace to resist movement.

US 2005/0043659 to Challis describes an apparatus for treating long bone fractures. An inflatable cuff is placed around the limb to provide compression of the fracture and surrounding musculature. Alternatively, electrical stimulation of the muscles may be used to compress the fracture.

GB 2 426 930 to Duncan describes a support for lower leg trauma patients which includes a base plate to provide support to the ankle, and electrical stimulation points to stimulate muscle contraction of the ankle and reduce muscle wastage.

GB 1 527 233 to Bleach describes an electrical stimulation device having a hollow shell which may be secured around the body part to be treated.

US 2007/0060975 to Mannheimer describes an electrical stimulation device operated as a TENS device for reducing pain, which may be used in combination with a splint, brace, bandage, or cast.

US 2004/0249432 to Cohen describes a surface electrode for skin stimulation of a patient.

U.S. Pat. No. 4,445,518 to Eggli describes a flexible areal electrode for use with a cast, and the use of holes in the cast and a filament for engaging with the electrode, designed to allow the electrode to be located within the cast.

SUMMARY OF THE INVENTION

According to a first aspect of the invention, there is provided a kit for improving blood circulation in a lower limb of a patient, the kit comprising:

a device comprising at least one electrode for administering an electrical stimulus to opposed leg muscles of a patient; a power supply connectable to the electrode; and a control means for activating the electrode to administer an electrical stimulus to the muscles sufficient to cause the muscles to contract isometrically; and a device for substantially immobilising a lower limb joint of a patient.

By isometric contraction is meant contraction of antagonistic and agonistic muscle groups simultaneously, or near simultaneously. In preferred embodiments of the invention, electrical stimulation of the lateral popliteal nerve allows stimulation of both anterior and posterior lower limb muscle groups with a single point of stimulation.

As noted above, we have surprisingly found that immobilising the joint to prevent limb movement results in an unexpected increase in improvement in blood circulation in the limb, including microcirculation, compared with stimulation without joint immobilisation. Without wishing to be bound by theory, we believe that this is because the muscles are required to work against the immobilisation as well as being electrically stimulated, thereby increasing muscle work beyond what is possible by electrical stimulation alone.

The kit may be useful in treatment of a variety of conditions. These include deep vein thrombosis (DVT), which is of particular concern when patients are immobilised for long periods of time. For certain patients, conventional DVT prophylaxis—such as anti coagulant drugs—is not possible, and so this may provide an alternative treatment. Certain conditions may increase the risk of acute compartment syndrome, particularly where the limb is inflamed and contained within a plaster cast; it is believed that treatment with the device may reduce inflammation and so reduce the risk of acute compartment syndrome and hence avoid the need for fasciectomy as an alternative treatment.

The kit may also be used to promote wound healing; for example, by increasing microcirculation near the site of broken bones; or to promote recovery from injury, in particular sports injuries which often relate to damage/disease to the metatarsals, tarsals, ankle and achilles tendon. Other potential uses include those described in our related patent applications WO2006/054118 and WO2010/070332.

Figure 1:
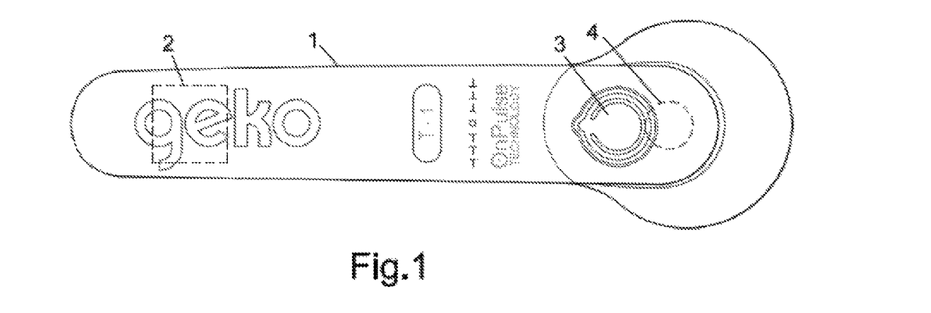
FIG. 1 depicts an electrical stimulation device.

The stimulation device and the immobilisation device may be integrated into a single device; for example, as a plaster cast or similar having integrated electrodes and the like. Alternatively, they may be provided as separate devices.

Where the devices are separate, the stimulation device may be for example as described in our WO2006/054118 and WO2010/070332. In a preferred embodiment, the device includes the electrodes 2, control means 3, and power supply 4 mounted on a flexible substrate 1 (e.g., as seen in FIG. 1). The substrate may be elongate. The device may further comprise a conductive gel or the like, and may include means for adhering the device to the limb of a patient. For example, the conductive gel may be adhesive.

Figures 2, 3:
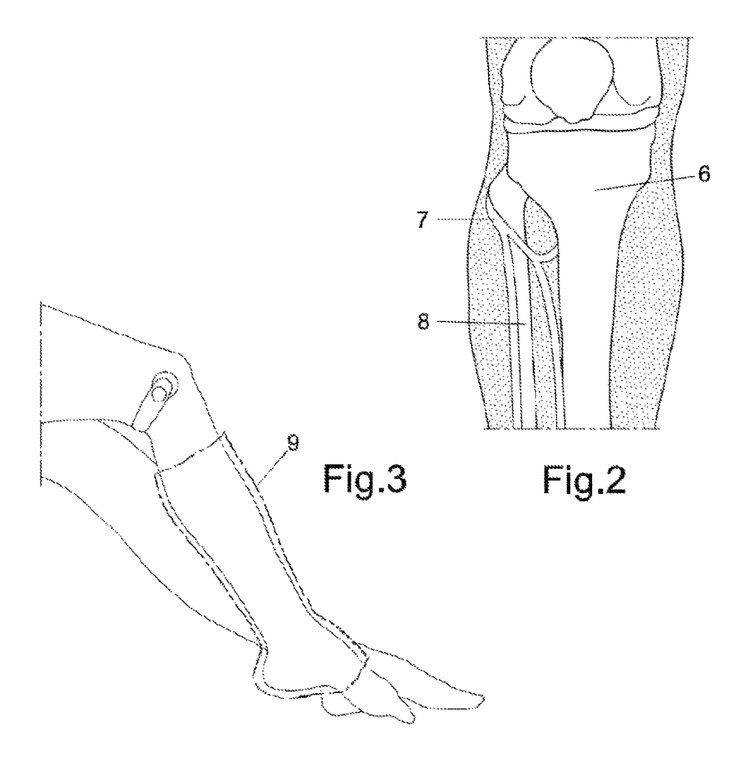
FIG. 2 depicts a human knee.
FIG. 3 depicts an electrical stimulation device and an immobilisation device.

The immobilization device 9 (as seen in FIG. 3) may be any suitable means for immobilising a joint. For example, an orthopedic cast or a plaster cast would be suitable, or an Aircast® style brace or boot, or the like. A brace or boot may include a pneumatic cushioning system to help immobilize the joint.

The site of immobilisation may depend on the nature of the condition to be treated. Typically the ankle will be immobilised, but where wound healing is to be promoted, the site of immobilisation may include that joint nearest the wound or fracture; for example, the knee may also or instead be immobilised.

The stimulus may be applied directly or indirectly to the muscle. The muscles may be calf muscles, or may be the ankle and/or foot musculature.

The control means is preferably a processor device having a stored program for activating the electrode.

The control means is preferably adapted to repeatedly activate the electrode.

The control means is preferably adapted to activate the electrode to deliver a current of between 0 to 100 mA, preferably 0 to 50 mA, more preferably 1 to 40 mA, and most preferably between 1 to 20 mA.

The control means may be adapted to activate the electrode to deliver an AC waveform, although preferably the control means is adapted to activate the electrode to deliver a DC waveform, more preferably a pulsed DC waveform. The waveform or pulse may have a frequency of 0.01 to 100 Hz, preferably 0.1 to 80 Hz, and most preferably 0.1 to 5 Hz. In other embodiments, the frequency may be 20 to 80 Hz, more preferably 30 to 60 Hz, and most preferably 40 to 50 Hz. Alternatively, a stimulus with a frequency from 0.1 to 1 Hz, or from 0.33 to 1 Hz may be used. The precise desired frequency may depend on the purpose of the method, and the general physical condition, age, sex, and weight of the patient, among other factors.

The control means preferably activates the electrode to deliver a stimulus for a duration between 0 and 1000 ms, between 100 and 900 ms, between 250 and 750 ms, between 350 and 650 ms, or between 450 and 550 ms. In certain embodiments, the stimulus may be applied for up to 5000 ms, up to 4000 ms, up to 3000 ms, or up to 2000 ms. Other durations may be used; again this may depend on the details of the patient.

The control means may be adapted to vary characteristics of the stimulus over time. For example, a single stimulus may increase in current over the duration of the stimulus. Preferably the increase is gradual up to a peak; the stimulus may then either be maintained at the peak; terminate at the peak; or decrease in a gradual manner. Alternatively, where repeated stimuli are applied, characteristics of the stimuli may vary between different stimuli. For example, successive stimuli may be applied at increasing levels of current. Again, these successive stimuli may increase up to a peak gradually, followed by maintenance at that peak, or decrease from the peak. A cycle of increasing stimuli may be repeated a number of times.

The device may comprise a plurality of electrodes for administering electrical stimuli to a leg muscle of a patient. The plurality of electrodes may be disposed linearly, such that in use the electrodes are disposed along the main (long) axis of a user's limb. The control means may be adapted to activate the electrodes to apply stimuli at a plurality of locations on the muscle. For example, stimuli may be applied along the main (long) axis of the leg. Such stimuli may be applied simultaneously, or preferably sequentially such that a 'wave' of stimuli proceeds along the leg. Preferably such a wave proceeds upward toward the body of the patient.

The device may comprise timing elements to integrate synchronous activation with components of the QRS complex of a measured electrocardiogram. The device may further comprise means for determining a QRS complex of a measured electrocardiogram; and may yet further comprise means for obtaining an electrocardiogram from a patient.

The device may comprise an array of electrodes. It is well established in conventional Functional Electrical Stimulation, when using direct nerve stimulation via superficial electrodes, that the current required to provide effective stimulation depends on the positioning of the electrodes. The closer the direct current path between electrodes passes to the nerve motor point in question, the less current is required. Similarly, a given current is more effective in eliciting a muscle contraction if it passes closer to the specific motor nerve point. This means that the effectiveness of a device comprising a simple pair of electrodes is highly dependent on the correct positioning of the electrodes. Advantageously, electrodes may be provided as an array, instead of a single pair. Arrays with complex geometries may be produced, for example using printed circuit techniques, by photo-etching, or by conductive ink printing, or by other techniques. The stimulator circuit can then address different pairs of electrodes in sequence, for example by means of a demultiplexer or analog switch. In one embodiment, the electrodes comprise 2 rows of electrodes. In sequence, each electrode is paired with its counterpart in the other row. Thus, the direct current path between electrodes moves incrementally as different pairs of electrodes are addressed. This effectively allows the device to scan across a region, so allowing the current path to pass very close to the optimum motor point when the optimum pair of electrodes is addressed. This makes the positioning of the device on the skin much less critical. The device may operate continuously in scanning mode for the duration of use. Thereby each time the limb is to be periodically stimulated, a sequence of pulses would be delivered to each electrode pair in turn. Alternatively, the device could be so arranged that an initial set-up after attaching the electrode included an identification of the optimum electrode pair. This could be achieved by user feedback, for example by pressing a button when the best contraction was achieved. Alternatively, the device may have the facility for measurement of blood clearance by PPG or other means; the device could identify the optimum electrode pair by this means. Having established the optimum electrode pair, it would then be possible to address specifically those electrodes during the periodic stimulation.

A further development of the above may comprise a 2-dimensional array of electrodes. A circuit could be produced by printed circuit technique, photoetching, conductive printing, or by other means, such that electrodes could be arranged into rows and columns 2-dimensionally. Thus, by addressing specific rows and columns by means of a demultiplexer or analog switch or other means, 2-dimensional electrode position can be selected. This provides the means for scanning as above, but in 2 dimensions to locate the optimum motor point. In one variation, the position of each electrode in the pair is addressable. In another variation, one electrode remains in a fixed position, but is paired with a 2-dimensionally selectable electrode, to allow positional control of the current path. For example, an 8×8 array, addressable by 16-bit demultiplexer or analog switch, provides for 64 selectable locations of current path.

In an alternative embodiment, a selectable array of positive electrodes may be arranged radially or spirally around a central negative electrode, or vice versa, to give segmentally scanning position of current path.

The stimulation device preferably comprises a second electrode for administering a stimulus to a shin muscle of a patient. A device with a single electrode may be possible, where the single electrode is sufficient to apply a stimulus to opposed muscles directly, or where the stimulus is applied to a single nerve location which stimulates opposed muscles. Preferably the control means is adapted to activate the second electrode simultaneously with the electrode for administering a stimulus to a calf muscle. Alternatively the leg muscle may be stimulated via the lateral popliteal nerve; advantageously contraction may be stimulated simultaneously to both anterior and posterior lower limb muscle groups.

The electrode(s) may be of a generally conventional type; for example, reusable type like some TENS applications or disposable electrodes of the type commonly used for ECG applications. The electrodes may be self-adhesive; repositionable; semi-adhesive; or may include a conductive gel for ensuring skin contact. Alternatively, the stimulation device may comprise a conductive gel, or may comprise an alternative conductive medium for interposing between the electrode and a user's skin. For example, the device may comprise a liner impregnated with a conductive gel or electrolyte for location between the electrode and a user. The liner may be conductive in restricted locations; for example, at a number of locations over the liner. This allows stimuli to be applied at a number of locations on a user's limb using only a single electrode.

A further aspect of the invention provides a device for improving blood circulation in a lower limb of a patient, the device comprising:
at least one electrode for administering an electrical stimulus to opposed leg muscles of a patient; a power supply connectable to the electrode; and a control means for activating the electrode to administer an electrical stimulus to the muscles sufficient to cause the muscles to contract isometrically; and
means for substantially immobilising a lower limb joint of a patient.

A further aspect of the invention provides a method for improving blood circulation in a lower limb of a patient, the method comprising:
substantially immobilising a lower limb joint of a patient; and
providing an electrical stimulus to opposed leg muscles of the patient sufficient to cause the muscles to contract isometrically.

DETAILED DESCRIPTION OF THE INVENTION

Deep vein thrombosis, or DVT, refers to formation of a blood clot within the deep veins. DVT commonly affects the leg veins (femoral, popliteal) or deep veins of pelvis. The majority of thrombi originate in the soleal veins and venous valve pockets.

Risk factors of DVT include the following: Age>40 years; Cancer (×7 increased risk); Trauma; Previous DVT or PE; Recent surgery—especially surgery of lower limb particularly hip or knee (40-84% risk); Obesity; Varicose veins; Oestrogen therapy (women); Immobility; Long Haul Flights—'Economy class Syndrome'.

The application of a plaster cast to limb fractures can increase DVT risk as a combination of factors. Trauma to lower limb; surgery of lower limb; and prolonged immobility, can all combine to increase the risk of DVT. There is a lack of evidence of the real risk, but it is estimated to be ~20%. DVT can often be asymptomatic, and there is a high risk of developing PE following DVT in plaster cast. The UK's National Institute for Clinical Excellence (NICE) offers the guideline that a high level of clinical vigilance and an effective thromboprophylaxis should be considered even in simple cast treatment. DVT incidence rates are especially high in surgical patients.

Current prophylaxis can be pharmacological or physical. Both of these have disadvantages. Pharmacological prophylaxis can be used in plaster casts, but the disadvantages include active bleeding; allergic reactions; risk of VTE persists for weeks or months after hospital discharge; drug interactions with several substances e.g. antibiotics, foods; and clinical supervision requires money and inconvenience. Current mechanical treatments (for example, intermittent pneumatic compression or graduated compression stockings) cannot be used in plaster casts, and where the treatment is possible, there are numerous disadvantages, including skin damage/pain/ulceration; uncomfortable to wear; the size may be impractical; weight; external power source necessity; poor compliance.

Direct electrical stimulation of lower limb muscles has been shown to be effective in significantly improving blood flow. With this in mind, we investigated whether electrical stimulation in combination with a plaster cast would be effective in reducing the risk of DVT.

An illustration of a geko® devise is shown in FIG. 1. Use was made of an electrical stimulation device referred to as the geko® device. This consists of a pair of electrodes 2 mounted on an elongate flexible strip 1, together with a power source 4 and a control device for actuating the electrodes 2. The device is a disposable neuromuscular stimulation device, which is applied externally to the lateral aspect of the knee in to the popliteal fossa. Prior to its application, the attachment area of the knee was exfoliated and wiped with the electrode preparation wipe. After 30 seconds, the device was secured slightly above the crease in the popliteal fossa. This enabled the device to stimulate the common peroneal nerve (also referred to as the lateral popliteal nerve) resulting in isometric contraction of lower limb musculature, as the nerve innervates both antagonistic and agonistic muscle groups.

Objectives

Primary objective: Examine the flow characteristics of deep venous flow in the leg veins using Doppler ultrasound imaging and how this flow is modified by the application of a plaster and with a geko™ device in healthy volunteers.

Secondary Objective: Evaluate microcirculatory blood flow changes, using Laser Doppler fluxmetry associated with cast-immobilisation and with the use of geko™ device.

Study Population: Healthy male and female Volunteers, aged 18-65 years. Sample Size: 10 volunteers.

Exclusion criteria: previous leg fracture (within last 12 months); previous venous thrombosis; family history of venous thrombosis; history of musculoskeletal disorders e.g. osteoarthritis, rheumatoid arthritis; history of neurological disorders e.g. stroke, multiple sclerosis; Chronic obesity (BMI>34); Pregnancy.

Application: Common Peroneal Nerve

Superficial electrical stimulation (1 Hz) applied to the common peroneal nerve located in the popliteal fossa. The appropriate location is shown in FIGS. 2 and 3.

Physiology: electrical stimulation proximal to bifurcation causes near-isometric compression of lower limb musculature, which activates venous muscle pump, leading to increased venous return, resulting in reduced stasis, which leads to a reduced risk of DVT.

Outcome 1: Femoral Vein Ultrasound

This was measured in four different leg positions: Supine; Leg Elevated at 20°; Standing (weight bearing); and Standing (non-weight-bearing). Each of these was used with two variables: plaster cast or no plaster cast; and geko active or geko inactive.

This gives 16 positions in total; with n=9 (data from one volunteer was excluded due to failure of ultrasound recordings). The positions are listed in Table 1 below:

TABLE 1

| POSITION NUMBER | SETTING |
|---|---|
| 1 | NO PLASTER CAST/GEKO OFF/SUPINE |
| 2 | NO PLASTER CAST/GEKO OFF/LEG ELEVATED |

TABLE 1-continued

| POSITION NUMBER | SETTING |
|---|---|
| 3 | NO PLASTER CAST/GEKO OFF/STANDING-WEIGHT BEARING |
| 4 | NO PLASTER CAST/GEKO OFF/STANDING-NONWEIGHT BEARING |
| 5 | NO PLASTER CAST/GEKO ON/SUPINE |
| 6 | NO PLASTER CAST/GEKO ON/LEG ELEVATED |
| 7 | NO PLASTER CAST/GEKO ON/STANDING-WEIGHT BEARING |
| 8 | NO PLASTER CAST/GEKO ON/STANDING-NONWEIGHT BEARING |
| 9 | PLASTER CAST/GEKO OFF/SUPINE |
| 10 | PLASTER CAST/GEKO OFF/LEG ELEVATED |
| 11 | PLASTER CAST/GEKO OFF/STANDING-WEIGHT BEARING |
| 12 | PLASTER CAST/GEKO OFF/STANDING-NONWEIGHT BEARING |
| 13 | PLASTER CAST/GEKO ON/SUPINE |
| 14 | PLASTER CAST/GEKO ON/LEG ELEVATED |
| 15 | PLASTER CAST/GEKO ON/STANDING-WEIGHT BEARING |
| 16 | PLASTER CAST/GEKO ON/STANDING-NONWEIGHT BEARING |

Measurements were taken after each volunteer spent 10 minutes in each position to allow for the blood flow changes and equilibrum. These measurements were taken with the geko™ device inactive and was then repeated after the geko™ had been active for 10 minutes.

The device was set to visible twitch of the lower limb musculature as detailed in the Manufacturer's instructions for use. The setting for individual was noted and same level of electrical stimulation was applied to the volunteer throughout the study in order to avoid irregularities in the result.

Following baseline measurements, a below knee orthopaedic cast was applied to immobilise one leg of the volunteer. The fibreglass-based material was used due to its ability to mould and dry quickly. On application of the cast, volunteer lay supine for 30 minutes to allow the cast to set and temperature beneath the cast to adjust, in order to avoid bias caused by initial OC induced-heat. The application and removal of the plaster cast followed routine clinical practice.

Once an OC was applied, measurements were taken in above four positions with the geko™ device inactive. The measurements were then repeated after the geko™ had been active for 5 minutes.

At the end of the assessment the OC was removed. Volunteer's leg was clinically assessed prior to discharge from the study.

PEAK VENOUS VELOCITY (cm/s) has been demonstrated to have a proportional relationship with VENOUS RETURN, which is a measurement for reduced STASIS and a reduced DVT risk.

Figure 4:
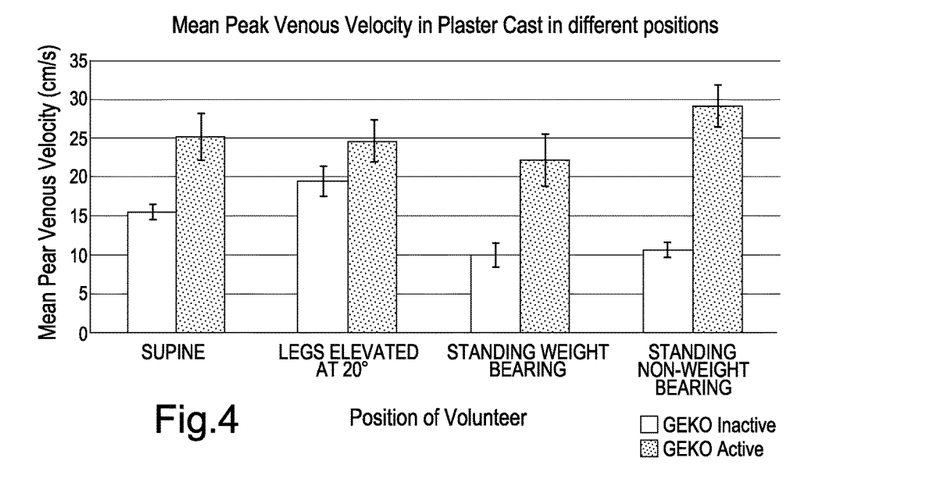
FIG. 4 is a graph showing measure results for mean peak venous velocity in patients' legs when immobilised by a plaster cast, with the patients in different positions, using the electrical stimulation device in an active state or inactive state.

The measured results for patients with a plaster cast are shown in FIG. 4.

The results for the four leg positions are as follows.

Supine:
Mean PVV=15.5 cm/s (sd=2.9)
Mean PVV=25.4 cm/s (sd=9.2)
1.8-fold increase in PVV when GEKO activated in supine position
Independent sample t-test: statistically significant ($P<0.05$)
Leg Elevated At 20°:
Mean PVV=19.5 cm/s (sd=6.2)

Mean PVV=24.6 cm/s (sd=8.4)

0.8-fold increase in PVV when GEKO activated in supine position

Independent sample t-test: statistically not significant (P>0.05)

Standing (Weight Bearing):

Mean PVV=9.9 cm/s (sd=4.9)

Mean PVV=22.3 cm/s (sd=8.4)

2.2-fold increase in PVV when GEKO activated in standing (weight bearing) position Independent sample t-test: statistically significant (P<0.05)

Standing (Non-Weight Bearing):

Mean PVV=10.7 cm/s (sd=3.1)

Mean PVV=29.3 cm/s (sd=8.5)

2.7-fold increase in PVV when GEKO activated in standing (weight bearing) position Independent sample t-test: statistically significant (P<0.05)

Figure 5:
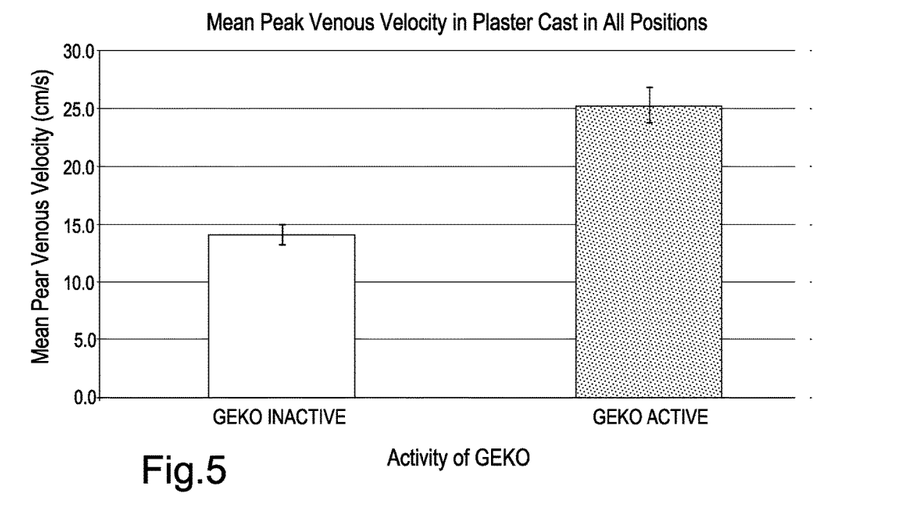
FIG. 5 is a graph showing measured mean peak venous velocity in patients' legs when immobilised by a plaster cast, with the patients in all positions, using the electrical stimulation device in an active state or inactive state.

FIG. 5 shows the combined results from all leg positions with a plaster cast.

Mean PVV in Plaster Cast when GEKO is inactive=14.2 cm/s (sd=5.4)

Mean PVV in Plaster Cast GEKO active=25.4 cm/s (sd=9.2)

1.8-fold increase in PVV in Plaster Cast across all 4 positions with GEKO active Independent sample t-test: statistically significant (P<0.05).

Thus, use of the geko device in combination with a plaster cast causes a statistically significant increase in peak venous velocity.

Outcome 2: Laser Doppler Fluxmetry 2 probes connect to the dorsal surface of the foot. n=10.

Figure 6:
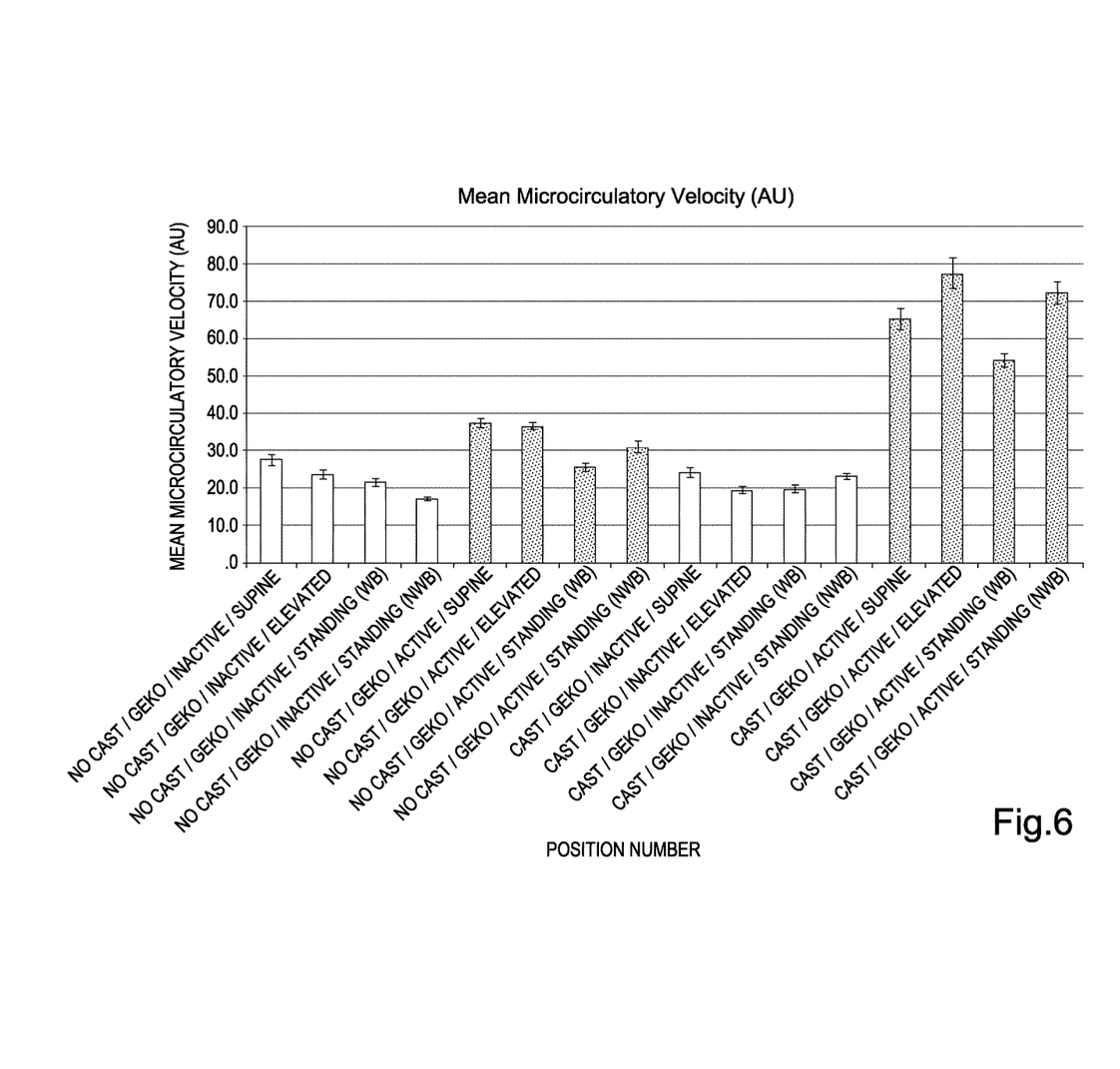
FIG. 6 is a graph showing measured mean microcirculatory velocity in the feet of patients, using the electrical stimulation device in an active state or inactive state, in different positions and under different experimental conditions.

FIG. 6 shows the mean microcirculatory velocity in the foot in all sixteen postural positions and experimental conditions.

The figure shows that Mean Microcirculatory Velocity in all four positions without the application of geko™ in a plaster cast=21.7 Arbitary Units (AU). Whereas Mean Microcirculatory Velocity in all four positions with the application of geko™ in a plaster cast=67.5 AU.

There is therefore a ~3-fold increase in Mean Microcirculatory Velocity when geko™ activated in a plaster cast. ANOVA, Post-hoc test (Bonferroni): statistically significant (p<0.05)

CONCLUSION

Primary Outcome: venous blood flow assessment: electrical stimulation to achieve isometric muscle contraction is effective in enhancing blood flow in the plaster cast, to a statistically significant degree (p<0.05). A potential clinical application may be mechanical DVT prophylaxis.

Secondary Outcome: microcirculatory blood flow assessment: electrical stimulation to achieve isometric muscle contraction is effective in enhancing microcirculatory blood flow to the skin in the plaster cast, to a statistically significant degree (p<0.05). Potential clinical applications include wound care healing (increased microcirculatory blood flow will reduce inflammation, promote phagocytosis and fibroblast stimulation); ulcer management; and sports injuries.

Stimulation of the common peroneal nerve proximal to bifurcation causes near-isometric compression of the lower limb musculature including peroneus longus muscle, a powerful foot everter. A cast confines the limb causing restricted foot eversion. As geko™ is activated in an immobilised limb, stimulation of the peroneus longus mucle combined with restricted eversion causes the plantar plexus to compress against the sole of the cast, emptying the venous plexus at a greater velocity. As increased lower limb PVV has been linked to improved venous return and reduce venous stasis, the risk of DVT reduces likewise.

In a cast, electrical stimulation of the lower limb caused the mean vessel diameter to increase (greater venodilation due to enhanced pressure caused by increased PVV). Electrical stimulation of the limb without the cast although, causes increased venous return (as indicated by the increased PVV) but the mean vessel diameter reduces. However, this relationship between mean PVV and mean vessel diameter is reversed when geko™ is activated without the OC application. This indicates stimulation of geko™ in an OC maybe causing more efficient emptying of venous plexus due to compression generated by the OC itself.

The invention claimed is:

1. A kit for improving blood circulation in a lower limb of a patient, the kit comprising:
a stimulation device comprising at least one electrode for administering an electrical stimulus to opposed leg muscles of a patient; a power supply connectable to the electrode; and a controller for activating the electrode to administer an electrical stimulus to the muscles sufficient to cause the muscles to contract isometrically; and
a below knee immobilisation device configured to eliminate motion in an ankle of a patient;
wherein the immobilisation device and the stimulation device are provided as separate devices such that the immobilisation device and the stimulation device are configured to couple to the patient independently of each other, and
wherein the stimulation device is configured to position the at least one electrode at the popliteal fossa of the patient.

2. The kit of claim 1 wherein the stimulation device includes the electrode, controller, and power supply mounted on a flexible substrate.

3. The kit of claim 1, wherein the immobilisation device comprises an orthopedic cast, a brace, or a boot.

4. A device for improving blood circulation in a lower limb of a patient, the device comprising:
a stimulation device comprising at least one electrode for administering an electrical stimulus to opposed leg muscles of a patient, a power supply connectable to the electrode, and a control means for activating the electrode to administer an electrical stimulus to the muscles sufficient to cause the muscles to contract isometrically, wherein the stimulation device is configured to position the at least one electrode at the popliteal fossa of the patient; and
means for eliminating motion in an ankle of a patient;
wherein said means for eliminating motion and said stimulation device are provided as separate devices such that the means for eliminating motion and the stimulation device are configured to couple to the patient independently of each other.

5. A method for improving blood circulation in a lower limb of a patient, the method comprising:
applying an immobilisation device to an ankle of the patient;
eliminating motion in the ankle of the patient using the immobilisation device;
attaching a stimulation device to a lower limb of the patient independent of the immobilisation device, wherein said stimulation device and said immobilisation device are provided as separate devices; and providing an electrical stimulus from the stimulation device to opposed leg muscles at the lateral popliteal nerve of the patient sufficient to cause the muscles to contract isometrically.

6. The device of claim 4, wherein the stimulation device includes an electrode, a controller, and a power supply mounted on a flexible substrate.

7. The device of claim 4, wherein the means for eliminating motion comprises an orthopedic cast, a brace, or a boot.

8. The method of claim 5, wherein the stimulation device includes an electrode, a controller, and a power supply mounted on a flexible substrate.

9. The method of claim 5, wherein the immobilisation device comprises an orthopedic cast, or a brace, or a boot.

* * * * *